United States Patent [19]

Kajdas et al.

[11] 4,311,036

[45] Jan. 19, 1982

[54] METHOD AND DEVICE FOR TESTING LUBRICATING PROPERTIES OF LUBRICATING MEANS

[75] Inventors: Czeslaw Kajdas, Plock; Jozef Nita, Radom; Krzysztof Krawczyk, Kielce, all of Poland

[73] Assignee: Politechnika Swietokrzyska, Kielce, Poland

[21] Appl. No.: 108,402

[22] Filed: Dec. 28, 1979

Related U.S. Application Data

[63] Continuation of Ser. No. 967,258, Dec. 5, 1978, abandoned.

[30] Foreign Application Priority Data

Dec. 10, 1977 [PL] Poland ............................. 202856

[51] Int. Cl.³ .............................................. G01N 19/00
[52] U.S. Cl. ...................................................... 73/10
[58] Field of Search .................................. 73/10, 9, 135

[56] References Cited

U.S. PATENT DOCUMENTS

| | | | |
|---|---|---|---|
| 2,031,253 | 2/1936 | Davis | 73/10 |
| 2,059,856 | 11/1936 | Eastman | 73/10 |
| 3,145,558 | 8/1964 | Borrino | 73/10 |
| 3,196,346 | 7/1965 | Inoue | 73/10 |

FOREIGN PATENT DOCUMENTS

2277342  1/1976  France ................................ 73/10

OTHER PUBLICATIONS

Catolog of Friction and Wear Devices; Benzing et al., pp. 8, 41, 45, 46, 51, 52, 121, 153, 157, 158, 200, 201, Aug. 1973.

"Standard Handbook for Mechanical Engineers", Baumeister and Marks, Seventh Edition, copyright 1967, pp. 3–34.

*Primary Examiner*—Charles A. Ruehl
*Assistant Examiner*—Denis E. Corr
*Attorney, Agent, or Firm*—Haseltine and Lake

[57] ABSTRACT

Method of testing the lubricating properties of the lubricating means consisting in that in a test master rubbing pair, operating at a definite temperature and with definite unit pressures, or at a definite temperature and with a definite rubbing speed, at the presence of the lubricating means being tested, either the slip rates are gradually decreased in a linear way, or the unit pressures are gradually increased also in a linear way and, at the same time, parameters characterizing these properties are recorded. The rubbing speed is gradually decreased down to a minimum limit value, or the unit pressures are gradually increased to a definite maximum limit value corresponding to a condition, when the electric resistance and the friction force attain the values characteristic for the dry friction.

In the device according to the invention the rotary test piece (1) is mounted on a shaft of an electric motor (2). Two counter-specimens are mounted in holders (5) accommodated in the insulating guideways (6) mounted in the device body (7), the said device consisting of an inner chamber (8) containing the lubricating means to be tested (9) and of an outer chamber (11) containing the thermostatic liquid (12). The motor housing (2) is connected to the body (7) by means of a ball bearing (13) and a spring element (14).

1 Claim, 2 Drawing Figures

METHOD AND DEVICE FOR TESTING LUBRICATING PROPERTIES OF LUBRICATING MEANS

This is a continuation of application Ser. No. 967,258 filed Dec. 5, 1978, now abandoned.

FIELD OF THE INVENTION

The present invention relates to a method and apparatus for testing the lubricating properties of lubricating means having antifriction, anti-wear and anti-seizure properties, said method and apparatus enabling the determination of the type of friction, as well as providing an accurate and quick measurement of all the essential parameters characterizing these properties.

PRIOR ART

The apparatus most often used include: four ball device, Timken machine, Almen machine, Amsler machine and SAE type device.

The four-ball device has four balls made of bearing steel which serve as frictional members. Three of these balls are immobilized and immersed in the lubricating means being tested. The fourth ball is mounted in a holder which is driven in rotary motion by means of an electric motor through a gear transmission with variable transmission ratio.

The rotary ball is loaded and rubs against the remaining three balls. The friction force and the ball wear depend upon the test load applied to the ball and upon the rotational speed of the ball, upon the lubricating means and its temperature. The device permits only the friction moment and the abrasion traces to be determined and ensures only comparative investigations. A further drawback of the device is a variable contact area of the frictional members in the course of the test as well as the fact that the frictional resistances being measured are distorted to some extent by loading of the supporting bearings in the measuring system. Moreover, the material of the balls is established once and for all and the same material only rarely is used in the gears in which the lubricant being tested is used.

In the Almen machine, the frictional member is in the form of a rotary driven steel shaft against which two steel half-bushes are pressed.

Both the shaft as well as the half-bushes are immersed in the lubricant being tested. Measurement is continued up to the seizure of the frictional members, that is to the destruction of a shaft at the notch therein. The frictional members can be made of various materials. The device makes possible the measurements of the seizing loading, friction force and temperature under the friction face, thus enabling comparative investigations to be performed, said comparative investigations being unfortunately not sufficiently accurate.

Another drawback of this device is a non-uniform distribution of unit pressures on the frictional areas resulting from the structural properties of the friction pair.

SUMMARY OF THE INVENTION

An object of the present invention is to provide a method and apparatus for the investigation of the lubricating means which do not have the drawbacks of the above mentioned prior art, ensuring investigations of the lubricating properties within the full range of friction, that is for lubricating means providing fluid friction between the tested bodies and boundry friction between the bodies. Moreover, the method and apparatus provide linear program control of the applied loads for investigating the lubricating means.

The principle of operation of the apparatus according to the present invention consists in applying the load in a linear manner with determined intensity, or linearly varying the rubbing speed of the tested objects in the presence of the lubricating means while simultaneously recording: friction force, temperature under the friction face, and electric resistance in the friction zone. Load application is characteristic for boundry friction.

The method according to the invention consists in carrying out two kinds of tests.

In the master test, the friction surfaces are operated at a definite temperature and with definite unit pressures in the presence of the lubricating means being tested and the rubbing speeds are gradually decreased linearlly and, at the same time, there are recorded the temperature rise under the friction face, friction forces and electrical resistance in the friction zone, the rubbing speed being gradually decreased to a minimum limit value corresponding to the condition when the electrical resistance of the friction zone and the friction force are characteristic of dry friction.

In the master test, the friction surfaces are operated at a definite temperature and with definite unit pressures in the presence of the lubricating means being tested, the unit pressures being increased linearly and the temperature rise, friction force and electric resistance within the friction zone are simultaneously measured, said unit pressures being increased until a maximum limit value is obtained corresponding to the condition when the electrical resistance and the friction force attain values characteristic of dry friction.

The apparatus for implementation of the method according to the present invention consists of three units namely, a friction pair units, a parameter adjustment and stabilization unit and a parameter measurement and recording unit.

The friction pair unit contains a pair of frictional members in the form of a known match, that is consisting of a rotary cylindrical ring and two counter-specimens located opposite each other. The rotary ring is mounted on a shaft of a driving motor. Both counter specimens are mounted in holders accommodated, in turn, in isolating guideways. Each counter-specimen holder can move in a longitudinal direction along its own axis but cannot revolve around this axis. Insulating guideways are mounted in the device body, consisting of an inner chamber containing the lubricating means being tested, and an outer chamber containing a thermostatic liquid. The driving motor for the rotary specimen is coupled with the body by means of a ball bearing and connected to this body by means of a spring member, on which strain gauges for the measurement of the friction force are cemented. Both counter-specimens holders project outside the insulating guideways and include terminal insulating inserts provided with holes accommodating cylindrically machined bolt ends with an external thread. The bolts are screwed into the end pieces of a dynamometer in the shape of a horseshoe, whereas on one of these bolts there is mounted a knob for a manual adjustment of the dynamometer stresses, the second bolt receiving drive from an electric motor via a worm transmission. In one of the counter-specimens there is mounted a temperature gauge just under frictional face, the said gauge being introduced through the counter-specimen holder. Another temperature gauge is located in the lubricating means and serves for the determination and, if necessary, stabilization of the temperature of said lubricating means.

The unit for adjustment and stabilization of parameters includes an adjuster and stabilizer of temperature of the lubricating means being tested. This adjuster and stabilizer is controlled by a temperature gauge located in the lubricating means. The rubbing speed of the friction pairs is adjusted and stabilized by means of the adjuster and stabilizer, whereas the loads in the friction unit are applied in an automatic manner according to an arbitrary program by means of an automatic pressure adjuster in the friction unit.

The system for the measurement and recording of parameters consists of three blocks and provides an accurate measurement of the value as well as a continuous and simultaneous record of electric resistance in the friction zone, friction force and temperature under the friction face.

BRIEF DESCRIPTION OF THE DRAWING

An embodiment of the present invention will now be described, by way of example, with reference to the accompanying drawing, wherein.

DETAILED DESCRIPTION

In a friction unit A containing a master test rubbing pair i.e. two frictional surfaces operating at a temperature determined by means of an adjuster and stabilizer of the temperature of the lubricating means I and a position determined by means of an automatic pressure adjuster II in the friction unit, the rubbing speeds are gradually decreased in linear fashion by means of an adjuster and stabilizer of the rubbing speeds III, and, at the same time, the electrical resistance within the friction zone is measured and recorded by means of a meter and recorder of electric resistance IV in the friction zone and, moreover, the friction force is measured and recorded by means of a suitable meter and recorder of friction force V. Additionally, the temperature increase at the frictional surfaces is measured and recorded by means of a meter and recorder of temperature rise VI at the friction surface. The master friction test unit is accommodated in the lubricating means i.e. lubricant to be tested.

In the rubbing pair unit A containing the master test rubbing pair operating at a temperature determined by means of an adjuster and stabilizer of the temperature of the lubricating means I and at rubbing speed determined by means of the adjuster and stabilizer of the rubbing speed III, the unit pressures are varied in a linear-increasing manner by means of the automatic pressure adjuster VI and, at the same time, electrical resistance within the friction zone is measured and recorded by means of the meter and recorder of electric resistance IV within the friction zone. Moreover, the friction force is measured and recorded by means of the meter the recorder of friction force V, and temperature increase at the frictional surfaces is recorded by means of the meter and recorder of temperature rise VI at the frictional surfaces. The master test rubbing pair is accommodated in the lubricant to be tested.

The described method is implemented by the device consisting of the three units:

rubbing pair unit A containing the master test rubbing pair, system B for adjustment and stabilization of parameters including: adjuster and stabilizer of the temperature of the lubricating means I, automatic pressure adjuster II of the friction pair, as well as the adjuster and stabilizer of the rubbing speed III in the rubbing pair, system C for the measurement and recording of parameters, including the meter and recorder of electrical resistance IV within the friction zone, the meter and recorder of the friction force V, and the meter and recorder VI of the temperature at the friction surfaces.

The rubbing pair unit A includes the master test rubbing pair with strictly determined parameters such as: dimensions, roughness classes of the friction faces, grade of material etc.

Figure 1:
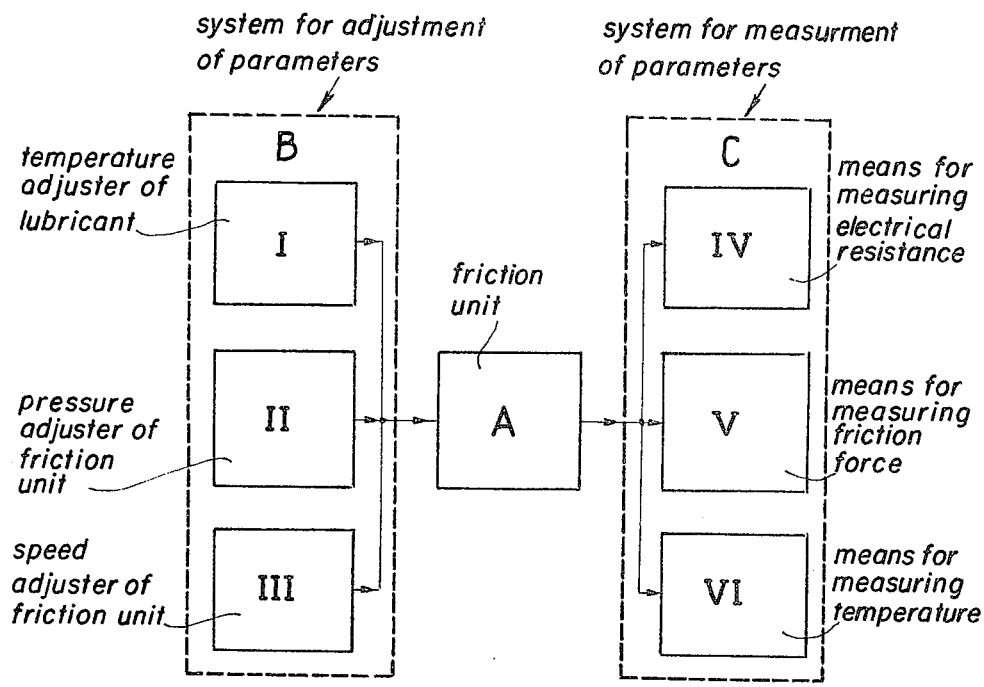
FIG. 1 is a block diagram of the instrument.
Figure 2:
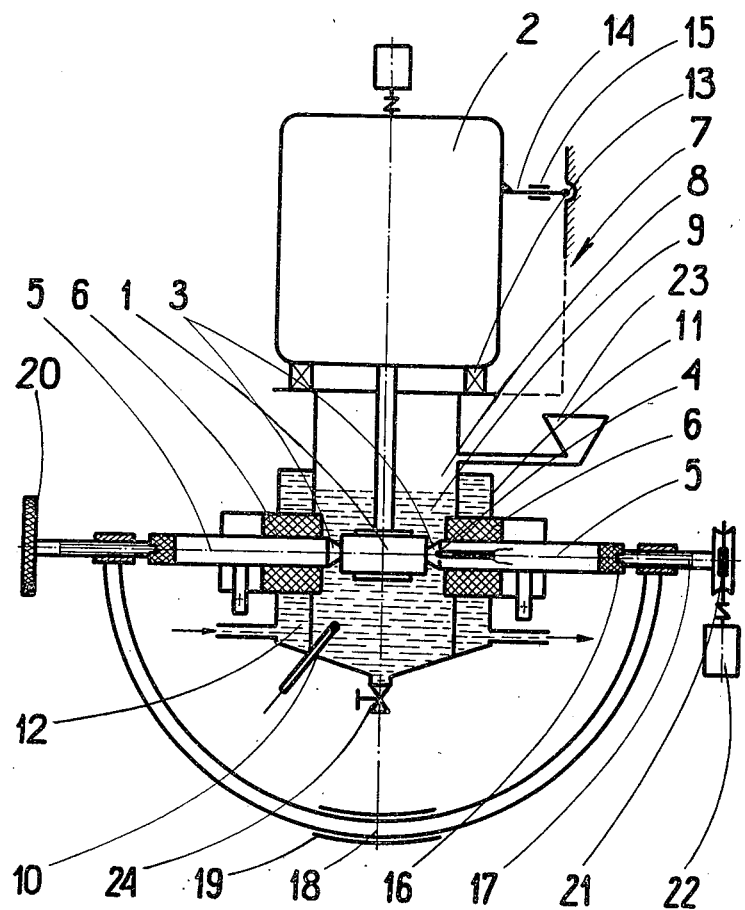
FIG. 2 is a diagrammatic illustration of the actuating unit containing the rubbing pair.

Known in the art is a rubbing pair consisting of a rotating test piece 1 in the shape of a ring and mounted on the shaft of driving electric motor 2 and two counter-specimens 3, one of said counter-specimens accommodating a temperature gauge 4; the counter-specimens 3 are mounted in suitable holders 5. According to the invention the area of the rubbing surfaces of the counter-specimen 3 is much smaller than in the prior art (compare FIG. 2) and this enables a constant contact-surface area during the testing and over the entire friction range. The rotary test piece 1 and one of the counter-specimens 3 include measuring cables of the meter and recorder of electrical resistance V within the friction zone. Holders 5 can be moved along their own axes but cannot revolve around them and are accommodated in insulating guideways 6 mounted in the body 7 of the device, said body consisting of an inner chamber 8 containing the lubricating means 9 to be tested, wherein temperature gauge 10 is located, and an outer chamber 11, containing thermostatic liquid 12. Driving motor 2 is mounted on the body 7 by means of a ball bearing 13 and through a spring element 14 with strain gauges 15 mounted thereon.

The holders 5 of counter-specimens 3, project from insulating guideways 6 and have insulating inserts 16 at their ends. The inserts 16 are provided with blind bores extending along the axes of holders 5 and accommodating the cylindrically machined end pieces of bolts 17 screwed into opposed branches of a half-ring dynamometer 18. One of the bolts 17 has a knob 20 for manual adjustment of the pressure of the dynamometer, the second bolt being connected via a worm transmission 21 to a driving step motor 22. Cemented on the half-ring dynamometer 18 are strain gauges for the loading of the measurement of the rubbing pair. The temperature gauge 4 extends through the holder 5 of the associated counter-specimen for the measurement of the temperature at the frictional surfaces, the other temperature gauge 10 measuring the temperature in the lubricating means 9. The lubricating means 9 being tested is introduced into the inner chamber 8 through a filler 23 and is discharged through valve 24.

What is claimed is:

1. Device for testing the lubricating properties of the lubricating means characteristic in that a rotary test piece (1) in the shape of a ring is mounted on the shaft of an electric motor (2) driving the said test piece, and two counter-specimens (3), one of which accommodates the temperature gauge (4), are mounted in holders (5), the said holders being located in insulating guideways (6) mounted in the device body (7), the said device consisting of an inner chamber (8) containing the lubricating means being tested (9) with a temperature gauge (10) located in it and an outer chamber (11), containing the thermostate liquid (12), whereas the motor housing (2) is connected to the body (7) by means of a ball bearing (13) and a spring element (14), whereon the strain gauges (15) are cemented, the both holders (5) of counter-specimens (3), within the portions of the insulating guideways (6) projecting outside, being terminated with the insulating inserts (16), whereas in the axes of holders (5) there are blind holes accommodating the end-portions of bolts (17), screwed into the end portion of dynamometer (18), made in the shape of a half-ring with the strain gauges cemented thereon, whereas on one of the said bolts (17) there is a knob (20) for a manual adjustment of stress of dynamometer (18), the second bolt (17) being driven by a step electric motor (22) via the worm transmission (21).

* * * * *